United States Patent
Mühlebach et al.

(10) Patent No.: US 7,157,537 B2
(45) Date of Patent: Jan. 2, 2007

(54) α-HALOGENATED ACID ESTERS WITH POLYVALENT ALCOHOLS AS ATOM TRANSFER RADICAL POLYMERIZATION INITIATORS

(75) Inventors: Andreas Mühlebach, Frick (CH); François Rime, Delémont (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 280 days.

(21) Appl. No.: 10/787,676

(22) Filed: Feb. 26, 2004

(65) Prior Publication Data

US 2004/0260051 A1    Dec. 23, 2004

Related U.S. Application Data

(63) Continuation-in-part of application No. 09/889,640, filed as application No. PCT/EP00/00097 on Jan. 10, 2000, now abandoned.

(30) Foreign Application Priority Data

Jan. 21, 1999  (CH) ........................ 107/99

(51) Int. Cl.
*C08F 118/02*   (2006.01)

(52) U.S. Cl. .................. 526/319; 526/324; 526/327; 526/329.2; 526/329.7

(58) Field of Classification Search ............... 526/319, 526/324, 327, 329.2, 329.7
See application file for complete search history.

(56) References Cited

U.S. PATENT DOCUMENTS 5,789,487 A * 8/1998 Matyjaszewski et al. ... 525/301

FOREIGN PATENT DOCUMENTS

DE          2232136          1/1974

OTHER PUBLICATIONS

Ueda et al., Macromolecules vol. 31, No. 3, (02) 1998 pp. 557-562.*
K. Matyjaszewski et al., Macromolecules, (1999), vol. 32, pp. 6526-6535.
J. Ueda et al., Macromolecules, (1998), vol. 31, No. 3, pp. 557-562.
G. E. McCasland et al., Journal Am. Chem. Soc., vol. 74, No. 2, pp. 564-565 (1952).
Derwent Abstr. 04247V/03 for DE 2232136 (1974).
T. Ziegler, Liebigs Ann. Chem. (1990), pp. 1125-1131.

* cited by examiner

*Primary Examiner*—Robert D. Harlan
(74) *Attorney, Agent, or Firm*—Joseph C. Suhadolnik

(57) ABSTRACT

The invention relates to α-halocarboxylic acid esters of polyhydric, at least trihydric, alcohols, which can be used as initiators for ATRP. Using those initiators it is possible to prepare block copolymers having branched structures.

4 Claims, No Drawings

α-HALOGENATED ACID ESTERS WITH POLYVALENT ALCOHOLS AS ATOM TRANSFER RADICAL POLYMERIZATION INITIATORS

This is a Continuation-In-Part of Application Ser. No. 09/889,640, filed on Jul. 19, 2001 now abandoned, which is the National Stage of International Application No. PCT/EP 00/00097, filed on Jan. 10, 2000.

The present invention relates to α-halocarboxylic acid esters with polyhydric alcohols, which can be used as initiators for ATRP, to processes for the preparation of such initiators, to polymers or copolymers that can be prepared using those initiators, to compositions comprising such polymers or copolymers, to processes for the preparation thereof and to the use thereof in the preparation of polymers or block copolymers wherein the terminal group .X is replaced by an open-chain or cyclic group R'R"N—O..

Atom Transfer Radical Polymerisation (ATRP) is a polymerisation process that has been known for a long time and is especially suitable for the preparation of "living" polymers, block copolymers, graft copolymers, etc. having low polydispersity and largely predeterminable molecular weights.

Despite their obvious advantages, such polymerisation processes have a disadvantage in that there is only a small selection of initiators suitable for the preparation of branched polymer structures. The known polymerisation initiators, which are described, for example, in WO 96/30421, e.g. 2-chloro- or 2-bromo-acetic acid or 2-chloro- or 2-bromo-isobutyric acid, result in linear, but not branched, structures of the polymer chain and therefore allow only a small structural variation in the polymers that can be obtained.

The problem underlying the present invention is to prepare polymerisation initiators suitable for the synthesis of branched polymer structures, e.g. star polymers, dendrimers, comb-shaped polymers, etc.. The problem is solved by the present invention, which relates to α-halocarboxylic acid esters with polyhydric alcohols that can be prepared by simple acylation processes.

The invention relates to α-halocarboxylic acid esters of formula

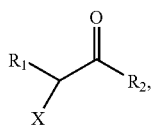

(I)

wherein
$R_1$ is hydrogen, $C_1$–$C_4$alkyl, cyano, phenyl or $C_1$–$C_4$alkylphenyl;
X is chlorine, bromine or iodine; and
$R_2$ is the radical of an acylated, branched, trihydric alcohol, the radical of a fully or partially acylated, linear or branched, tetrahydric alcohol, the radical of a fully or partially acylated, linear, penta- or hexa-hydric alcohol, the radical of a fully or partially acylated, linear or cyclic $C_4$–$C_6$aldose or $C_4$–$C_6$ketose or the radical of a fully or partially acylated disaccharide, and to isomers of such compounds.

The terms and nomenclature used in the description of the present invention are preferably defined as follows:

$C_1$–$C_4$Alkyl is methyl, ethyl, n-propyl or isopropyl or n-, sec- or tert-butyl.
$C_1$–$C_4$Alkylphenyl is preferably p-methylphenyl.
X is preferably chlorine or bromine.
$R_1$ preferably forms with the α-carbon atom a 2-haloacyl group, e.g. 2-halo-$C_3$–$C_4$alkanoyl, e.g. 2-halopropionyl, 2-halo-n-butyryl or 2-halo-isobutyryl, e.g. 2-chloro- or 2-bromo-propionyl or α-chloro- or α-bromo-isobutyryl, or an α-halophenylacetyl group, e.g. α-chloro- or α-bromo-phenyl acetate.

The radical $R_2$ of an acylated, branched, trihydric alcohol is preferably derived from 1,3,5-trihydroxybenzene or trimethylolethane and is, for example, a group of the partial formula

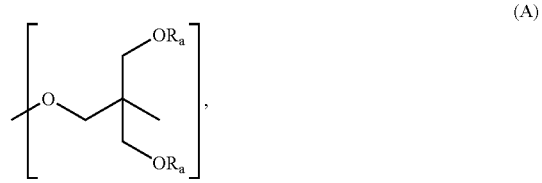

(A)

wherein $R_a$ is α-haloacyl. $R_a$ having the meaning α-haloacyl preferably denotes identical

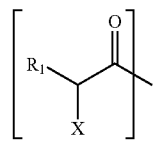

groups of the partial formula, e.g. α-halo-$C_3$–$C_4$alkanoyl or α-halo-phenylacetyl, e.g. α-chloropropionyl, α-bromopropionyl or α-chlorophenylacetyl.

The radical $R_2$ of a fully or partially acylated, linear tetrahydric alcohol is derived, for example, from erythritol and its 3 isomeric forms, e.g. D-, L- and meso-erythritol.

The radical $R_2$ is preferably derived from a fully or partially acylated, branched tetrahydric alcohol, e.g. from pentaerythritol, and is, for example, a group of the partial formula

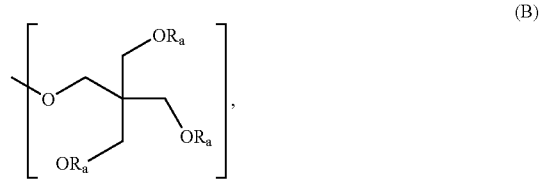

(B)

wherein $R_a$ is α-haloacyl having the meanings mentioned.

The radical of a fully or partially acylated, linear, penta- or hexa-hydric alcohol is derived, for example, from linear pentitols, such as D(+)- and L(−)-arabitol, adonitol or xylitol, or from linear hexitols, such as D-sorbitol, D-mannitol or dulcitol, all or some of the hydroxy groups of which are substituted by $R_a$(=α-haloacyl).

The radical of a fully or partially acylated, linear or cyclic $C_4$–$C_6$aldose or $C_5$–$C_6$ketose is derived, for example, from $C_4$aldoses, such as D(−)- and L(+)-erythrose or D(−)- and L(+)-threose, $C_5$aldoses, such as D(−)- and L(+)-arabinose, D(−)-ribose or D(+)-xylose, $C_6$aldoses, such as D(+)-glucose, D(+)-mannose or D(+)-galactose, or from a $C_6$ketose, such as fructose or L(−)-sorbose, and epimeric forms thereof, wherein all or some of the hydroxy groups are likewise substituted by $R_a$(=α-haloacyl).

The radical of a fully or partially acylated disaccharide is derived, for example, from saccharose, lactose or maltose, all or some of the hydroxy groups of which are likewise substituted by $R_a$(=α-haloacyl).

The term "isomeric forms" encompasses the forms of isomerism known in the chemistry of sugar alcohols and carbohydrates, e.g. the optically pure stereoisomers (antipodes), diastereoisomers or epimers or racemic mixtures.

A preferred embodiment of the invention relates to α-halocarboxylic acid esters (I) wherein $R_1$ is $C_1$–$C_3$alkyl or phenyl;

X is chlorine or bromine and $R_2$ is the radical of an acylated, branched, trihydric alcohol, e.g. the $R_a$-acylated radical of 1,3,5-trihydroxybenzene or trimethylolethane, the radical of a fully or partially acylated, linear or branched, tetrahydric alcohol, e.g. the radical of pentaerythritol fully acylated by $R_a$, or the radical of a fully or partially acylated, linear, penta- or hexa-hydric alcohol, and to isomers of such compounds.

In those preferred embodiments, $R_a$ has the meaning α-haloacyl, especially the meaning α-chloropropionyl or α-bromopropionyl.

An especially preferred embodiment relates to α-halocarboxylic acid esters of formula

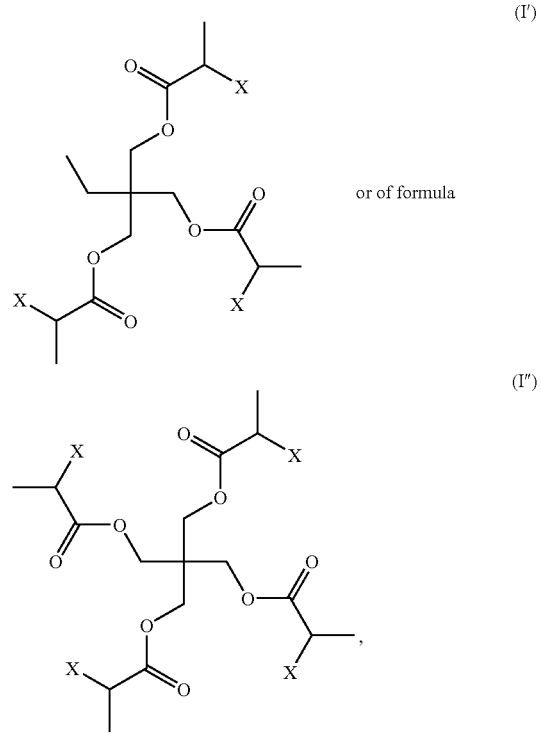

where in X is bromine or iodine.

The invention relates also to a process for the preparation of the α-halocarboxylic acid ester (I), wherein $R_1$, $R_2$ and X are as defined above, in which process an α-halocarboxylic acid of formula

or a reactive, functional acid derivative thereof, is reacted with an alcohol

or with a reactive alcohol derivative, wherein $R_2'$ together with the OH group forms a branched, trihydric alcohol, a linear or branched, tetrahydric alcohol, a linear, penta- or hexa-hydric alcohol, a linear or cyclic $C_4$–$C_6$aldose or $C_4$–$C_6$ketose or a disaccharide, and isomers of such compounds.

For the preparation of the α-halocarboxylic acid ester (I) there are used the customary methods of esterification, in which, for example, the equivalents of a reactive functional acid derivative of the α-halocarboxylic acid (II), for example an acid halide, e.g. the acid chloride, which correspond to the valence of the alcohol (III), are reacted with that alcohol, or the α-halocarboxylic acid (II) is reacted with the equivalents of a reactive functional derivative of the alcohol (III), for example with an ester of that alcohol, e.g. a halide, e.g. chloride, or with a sulfonic acid ester of the alcohol, e.g. with the p-toluenesulfonic acid ester.

The invention relates also to a polymer or block copolymer of formula:

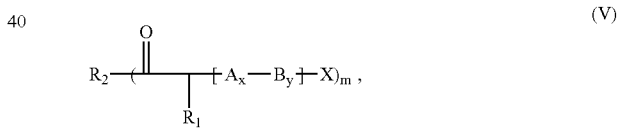

wherein $R_1$ is hydrogen, $C_1$–$C_4$alkyl, cyano, phenyl or $C_1$–$C_4$alkylphenyl;

$R_2$ is the radical of an acylated, branched, trihydric alcohol, the radical of a fully or partially acylated, linear or branched, tetrahydric alcohol, the radical of a fully or partially acylated, linear, penta- or hexa-hydric alcohol, the radical of a fully or partially acylated, linear or cyclic $C_4$–$C_6$aldose or $C_4$–$C_6$ketose or the radical of a fully or partially acylated disaccharide;

A and B are polymer blocks of ethylenically unsaturated monomer units;

x and y denote the number of monomer units in the blocks A and B, one value of x and y being zero and the other value being an integer greater than zero, or both values x and y being integers greater than zero;

X is chlorine, bromine or iodine; and m denotes an integer from three to six.

The invention relates also to a process for the preparation of the polymer or block copolymer (V), wherein $R_1$, $R_2$, A, B, X, x, y and m are as defined above, in which process ethylene-group-containing aliphatic monomers that form the basis of the polymer blocks A and B are subjected to a polymerisation reaction by atom transfer radical polymerisation (ATRP) in the presence of the α-halocarboxylic acid ester (I) as polymerisation initiator, wherein $R_1$, $R_2$ and X are as defined above, and in the presence of an oxidisable transition metal complex catalyst.

The term "polymer" encompasses oligomers, co-oligomers, polymers and copolymers, for example block copolymers, multiblock copolymers, star, gradient, random, branched and dendritic copolymers and graft copolymers. The copolymer blocks A and B comprise at least two structural repeating units of polymerisable, aliphatic monomers having at least one or more olefinic double bonds.

Such polymerisable, aliphatic monomers having an olefinic double bond are selected, for example, from the group comprising styrenes, acrolein, acrylic acid or methacrylic acid or salts thereof, acrylic acid or methacrylic acid anhydrides, acrylic acid or methacrylic acid $C_1$–$C_{24}$alkyl esters, acrylic acid or methacrylic acid mono- or di-$C_1$–$C_4$alkylamino-$C_2$–$C_4$alkyl esters, acrylic acid or methacrylic acid hydroxy-$C_2$–$C_4$alkyl esters, acrylic acid or methacrylic acid ($C_1$–$C_4$alkyl)$_3$silyloxy-$C_2$–$C_4$alkyl esters, acrylic acid or methacrylic acid ($C_1$–$C_4$alkyl)$_3$silyl-$C_2$–$C_4$alkyl esters, acrylic acid or methacrylic acid heterocyclyl-$C_2$–$C_4$alkyl esters, acrylic or methacrylic acid esters containing poly-$C_2$–$C_4$alkylene glycol ester groups, which may themselves be esterified by substituted $C_1$–$C_{24}$alkoxy groups, acrylic acid or methacrylic acid amides, acrylic acid or methacrylic acid mono- or di-$C_1$–$C_4$alkylamides, acrylic acid or methacrylic acid amino-$C_2$–$C_4$alkylamides and acrylonitrile.

Suitable styrenes can be substituted on the phenyl group by from one to three substituents from the group comprising hydroxy, $C_1$–$C_4$alkoxy, e.g. methoxy or ethoxy, halogen, e.g. chlorine, amino and $C_1$–$C_4$alkyl, e.g. methyl or ethyl.

Suitable salts of acrylic acid or methacrylic acid are, for example, ($C_1$–$C_4$alkyl)$_4$ammonium or ($C_1$–$C_4$alkyl)$_3$NH salts, e.g. the tetramethyl-, tetraethyl-, trimethyl-ammonium or triethyl-ammonium salt, the trimethyl-2-hydroxyethylammonium or triethyl-2-hydroxyethyl-ammonium salt, the dimethyl-2-hydroxyethylammonium or diethyl-2-hydroxyethylammonium salt.

Suitable acrylic acid or methacrylic acid $C_1$–$C_{24}$alkyl esters are esterified, for example, by methyl, ethyl, n-butyl, isobutyl, tert-butyl, 2-ethylhexyl, isobornyl, isodecyl, lauryl, myristyl, stearyl or behenyl.

Examples of acrylic acid and methacrylic acid mono- or di-$C_1$–$C_4$alkylamino-$C_2$–$C_4$alkyl esters are acrylic acid or methacrylic acid 2-monomethylaminoethyl ester, acrylic acid or methacrylic acid 2-dimethylaminoethyl ester or the corresponding 2-monoethylaminoethyl ester or 2-diethylaminoethyl ester and the acrylic acid or methacrylic acid 2-tert-butyl-aminoethyl ester.

Examples of acrylic acid and methacrylic acid hydroxy-$C_2$–$C_4$alkyl esters are acrylic acid or methacrylic acid 2-hydroxyethyl ester (HEA, HEMA) or acrylic acid or methacrylic acid 2-hydroxypropyl ester (HPA, HPMA).

Examples of acrylic acid and methacrylic acid silyloxy-$C_2$–$C_4$alkyl esters are acrylic acid or methacrylic acid 2-trimethylsilyloxyethyl ester (TMS-HEA, TMS-HEMA). Examples of acrylic acid or methacrylic acid ($C_1$–$C_4$alkyl)$_3$silyl-$C_2$–$C_4$alkyl esters are acrylic acid or methacrylic acid 2-trimethylsilylethyl ester or acrylic acid or methacrylic acid 3-trimethylsilyl-n-propyl ester.

Acrylic or methacrylic acid esters containing poly-$C_2$–$C_4$alkylene glycol ester groups, which may themselves be esterified by substituted $C_1$–$C_{24}$alkoxy groups, correspond to the formula:

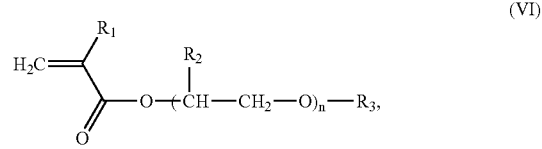

(VI)

wherein $R_1$ and $R_2$ are each independently of the other hydrogen or methyl and $R_3$ is $C_1$–$C_{24}$-alkyl, e.g. methyl, ethyl, n- or iso-propyl, n-, iso-, or tert-butyl, n- or neo-pentyl, lauryl, myristyl or stearyl, or aryl-$C_1$–$C_{24}$alkyl, e.g. benzyl or phenyl-n-nonyl, and $C_1$–$C_{24}$alkylaryl or $C_1$–$C_{24}$alkylaryl-$C_1$–$C_{24}$alkyl.

Examples of acrylic acid and methacrylic acid heterocyclyl-$C_2$–$C_4$alkyl esters are acrylic acid or methacrylic acid 2-(N-morpholinyl, 2-pyridyl, 1-imidazolyl, 2-oxo-1-pyrrolidinyl, 4-methyl-piperidin-1-yl or 2-oxoimidazolidin-1-yl)-ethyl esters.

Examples of the mentioned acrylic acid or methacrylic acid mono- or di-$C_1$–$C_4$alkylamides, acrylic acid or methacrylic di-$C_1$–$C_4$alkylamino-$C_2$–$C_4$alkylamides and acrylic acid or methacrylic acid amino-$C_2$–$C_4$alkylamides are N,N-dimethylacrylamide, N,N-dimethyl-(meth)acrylamide, 2-(N,N-dimethylaminoethyl)acrylamide, 2-(N,N-dimethylamino-ethyl)methacrylamide, 2-aminoethylacrylamide and 2-aminoethylmethacrylamide.

The indices x and y define the number of monomer units in the blocks A and B, one value of x and y being zero and the other value being an integer greater than zero, or both values x and y being integers greater than zero. For x and y, a number range of from 2 to 1000 is preferred.

In a block copolymer (V) the preferred molecular weight range of the blocks A and B is about from 1000 to 100,000, especially about from 1000 to 50,000. An especially preferred molecular weight range is about from 2000 to 15,000.

An especially preferred embodiment of the invention relates to a block copolymer (V)

wherein $R_1$ is $C_1$–$C_3$alkyl or phenyl;

X is chlorine or bromine and $R_2$ is the radical of an acylated, branched, trihydric alcohol, the radical of an acylated, linear or branched, tetrahydric alcohol or the radical of a fully or partially acylated, linear, penta- or hexa-hydric alcohol;

A and B are polymer blocks of ethylenically unsaturated monomer units;

x and y denote integers greater than zero and represent the number of monomer units in the blocks A and B; and m is three or four.

The invention relates also to all the polymers or block copolymers that can be prepared using α-halocarboxylic acid esters (I) and the ATRP method. The invention relates to all the products-by-process, even where they do not come under the definitions of formula V above or where formula V does not correctly define the structure of the products-by-process.

In a block copolymer (V), X is chlorine, bromine or iodine in the terminal position of the polymer chain. Those terminal groups are obtained using initiators according to the ATRP method. Halogen as the terminal group of a polymer chain can be disadvantageous. It is therefore possible, in a subsequent step, to replace halogen by other suitable terminal groups that are derived from TEMPO (=2,2,6,6-tetramethylpiperidyl-1-oxides) and derivatives thereof and have a structure of the following partial formula:

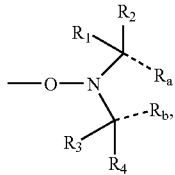
(A₀)

wherein one of $R_1$ and $R_2$ is $C_1$–$C_7$alkyl and the other is $C_1$–$C_4$alkyl or $C_1$–$C_4$alkyl substitute by $C_1$–$C_4$-alkoxycarbonyl or by $C_1$–$C_4$alkoxy; or $R_1$ and $R_2$ together with the adjacent carbon atom are $C_3$–$C_7$cycloalkyl;

$R_3$ and $R_4$ have the meanings of $R_1$ and $R_2$;

$R_a$ is $C_1$–$C_4$alkyl, cyano, $C_1$–$C_4$alkoxycarbonyl, $C_1$–$C_4$alkanoyloxy, $C_1$–$C_4$alkanoyloxy-$C_1$–$C_4$-alkyl, carbamoyl, mono- or di-$C_1$–$C_4$alkylcarbamoyl, mono- or di-2-hydroxyethylcarbamoyl, amidino, 2-imidazolyl, 1-hydroxy-2-hydroxymethyl-2-propylcarbamoyl or 1,1-dihydroxy-methyl-2-hydroxycarbamoyl; and $R_b$ has the meanings of $R_a$; or $R_a$ and $R_b$ together form a bivalent group and an aliphatic or aromatic heterocyclic group having 5, 6, 7 or 8 ring members, which can contain from 1 to 3 additional hetero atoms from the group nitrogen, oxygen and sulfur.

A preferred embodiment includes a group of the partial formula:

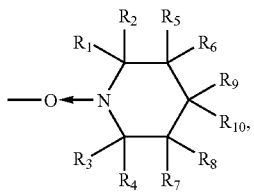
(A₁)

which can be substituted in the 4-position by one or two substituents. In the partial formula $A_1$ $R_1$, $R_2$, $R_3$ and $R_4$ are $C_1$–$C_4$alkyl;

$R_5$, $R_6$, $R_7$ and $R_8$ are hydrogen; and one of the radicals $R_9$ and $R_{10}$ each independently of the other denotes hydrogen or further substituents.

Representative examples of groups of the partial formula $A_1$ are the groups

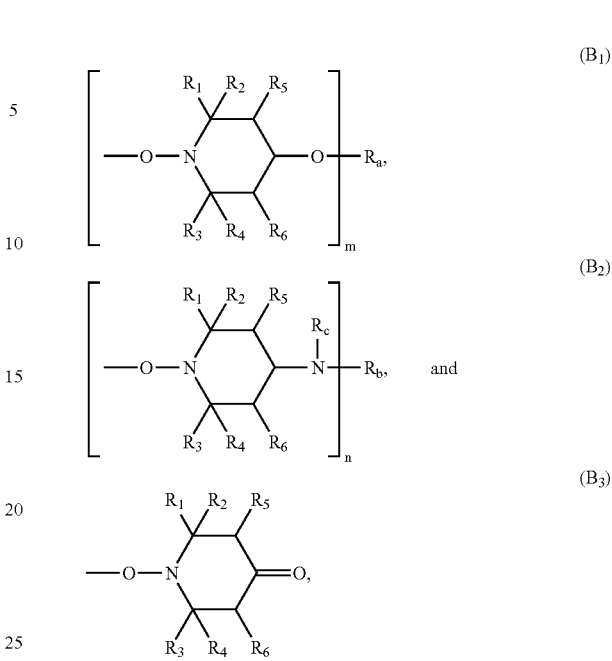

wherein m is 1;

$R_a$ is hydrogen, $C_1$–$C_{18}$alkyl, which can be interrupted by one or more oxygen atoms, 2-cyanoethyl, benzoyl, glycidyl, or the acyl group of an aliphatic $C_2$–$C_{12}$carboxylic acid, of a cycloaliphatic $C_7$–$C_{15}$carboxylic acid, of an a,b-unsaturated $C_3$–$C_5$carboxylic acid or of an aromatic $C_7$–$C_{15}$carboxylic acid;

m is 2;

$R_a$ is the bivalent acyl group of an aliphatic $C_2$–$C_{36}$dicarboxylic acid;

n is 1;

$R_b$ is $C_1$–$C_{12}$alkyl, $C_5$–$C_7$cycloalkyl, $C_7$–$C_8$aralkyl, $C_2$–$C_{18}$alkanoyl, $C_3$–$C_5$alkenoyl or benzoyl; and $R_c$ is $C_1$–$C_{18}$alkyl, $C_5$–$C_7$cycloalkyl, $C_2$–$C_8$alkenyl, which can be substituted by cyano, carbonyl or by a carbamide group, glycidyl, or a group of the partial formula —CH₂CH(OH)-Z, —CO-Z or —CONH-Z, wherein Z is hydrogen, methyl or phenyl.

A further preferred embodiment relates to a group of partial formula $A_1$ wherein one of the groups $R_9$ and $R_{10}$ is hydrogen and the other is $C_1$–$C_4$alkanoyl or $C_1$–$C_4$alkanoylamino.

The invention relates also to an N→O-substituted polymer or block copolymer of formula:

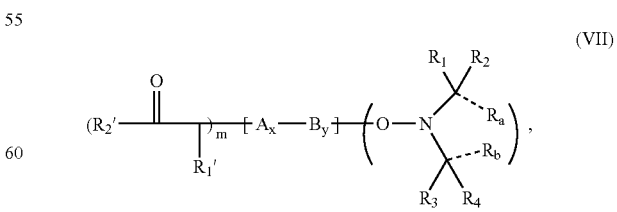
(VII)

wherein $R_1$ is hydrogen, $C_1$–$C_4$alkyl, cyano, phenyl or $C_1$–$C_4$alkylphenyl;

$R_2$ is the radical of an acylated, branched, trihydric alcohol, the radical of a fully or partially acylated, linear or branched tetrahydric alcohol, the radical of a fully or partially acylated, linear, branched or cyclic, penta- or hexa-hydric alcohol, the radical of a fully or partially acylated, linear or cyclic $C_4$–$C_6$aldose or $C_4$–$C_6$ketose or the radical of a fully or partially acylated disaccharide;

A and B are polymer blocks of ethylenically unsaturated monomer units;

x and y denote the number of monomer units in the blocks A and B, one value of x and y being zero and the other value being an integer greater than zero, or both values x and y being integers greater than zero;

X is chlorine, bromine or iodine;

m denotes an integer from three to six;

one of $R_1$ and $R_2$ is $C_1$–$C_7$alkyl and the other is $C_1$–$C_4$alkyl or $C_1$–$C_4$alkyl substituted by $C_1$–$C_4$-alkoxycarbonyl or by $C_1$–$C_4$alkoxy; or $R_1$ and $R_2$ together with the adjacent carbon atom are $C_3$–$C_7$cycloalkyl;

$R_3$ and $R_4$ have the meanings of $R_1$ and $R_2$;

$R_a$ is $C_1$–$C_4$alkyl, cyano, $C_1$–$C_4$alkoxycarbonyl, $C_1$–$C_4$alkanoyloxy, $C_1$–$C_4$alkanoyloxy-$C_1$–$C_4$-alkyl, carbamoyl, mono- or di-$C_1$–$C_4$alkylcarbamoyl, mono- or di-2-hydroxyethylcarbamoyl, amidino, 2-imidazolyl, 1-hydroxy-2-hydroxymethyl-2-propylcarbamoyl or 1,1-dihydroxy-methyl-2-hydroxycarbamoyl; and $R_b$ has the meanings of $R_a$; or $R_a$ and $R_b$ together form a bivalent group and an aliphatic or aromatic heterocyclic group having 5, 6, 7 or 8 ring members, which can contain from 1 to 3 additional hetero atoms from the group nitrogen, oxygen and sulfur.

The polymerisation process can be carried out in the presence of water or an organic solvent or mixtures thereof. Additional co-solvents or surfactants, for example glycols or ammonium salts of carboxylic acids, may be added to the reaction mixture. The amount of solvent should be kept as small as possible. The reaction mixture can contain the above-mentioned monomers or oligomers in a concentration of from 1.0 to 99.9% by weight, preferably from 5.0 to 99.9% by weight, especially from 50.0 to 99.9% by weight, based on the monomer content in the polymerisate.

Suitable organic solvents include alkanes (hexane, heptane, octane, isooctane), hydrocarbons (benzene, toluene, xylene), halogenated hydrocarbons (chlorobenzene), alkanols (methanol, ethanol, ethylene glycol, ethylene glycol monomethyl ether), esters (ethyl acetate) or ethers (diethyl ether, dibutyl ether, ethylene glycol dimethyl ether, tetrahydrofuran) or mixtures thereof.

When using water as solvent, it is possible to add to the reaction mixture a water-miscible or hydrophilic solvent. In doing so, care should be taken to ensure that during the polymerisation reaction the reaction mixture remains in a single homogeneous phase and no precipitation or phase separation occurs. Suitable co-solvents are selected from the group of aliphatic alcohols, glycols, ethers, glycol ethers, pyrrolidines, N-alkylpyrrolidinones, polyethylene glycols, polypropylene glycols, amides, carboxylic acids and salts thereof, esters, organosulfides, sulfoxides, sulfones, alcohol derivatives, hydroxyether derivatives, e.g. butylcarbitol or Cellosolve, amino-alcohols, ketones, derivatives and mixtures thereof, e.g. methanol, ethanol, propanol, dioxane, ethylene glycol, propylene glycol, diethylene glycol, glycerol, dipropylene glycol, tetrahydrofuran and other water-soluble or water-miscible solvents or mixtures thereof.

Hydrophilic monomers, polymers and copolymers can be separated from the reaction mixture using customary processes, for example by distillation, precipitation, extraction, alteration of the pH range or other customary methods of separation. The temperature range for the polymerisation reaction is from about 50° C. to about 180° C., preferably about from 80° C. to 150° C.

The oxidisable transition metal complex catalyst that can be used in the ATRP process is in the form of an oxidisable complex ion in the lower state of a redox system. Preferred examples of such redox systems are composed of elements of groups V(B), VI(B), VII(B), VIII, IB and IIB of the Periodic Table, e.g. redox systems of $Cu^+/Cu^{2+}$, $Cu^0/Cu^+$, $Fe^0/Fe^{2+}$, $Fe^{2+}/Fe^{3+}$, $Cr^{2+}/Cr^{3+}$, $Co^+/Co^{2+}$, $Co^{2+}/Co^{3+}$, $Ni^0/Ni^+$, $Ni^{+/Ni2+}$, $Ni^{2+}/Ni^{3+}$, $Mn^0/Mn^{2+}$, $Mn^{2+}/Mn^{3+}$, $Mn^{3+}/Mn^{4+}$ or $Zn^+/Zn^{2+}$. The transition metal or transition metal cation in the oxidisable transition metal complex catalyst is converted from the lower state of oxidation to a higher state of oxidation. In a preferred embodiment of the process, a Cu(I) complex catalyst salt is converted to the corresponding Cu(II) state of oxidation.

The oxidisable transition metal complex catalyst that can be used in the ATRP process can be prepared in a separate preliminary step or preferably in situ from the ligands and a metal salt, e.g. Cu(I)Cl, which is then converted to the complex compound by the addition of the ligand-former, e.g. ethylenediamine, EDTA, $Me_6TREN$ or PMDETA.

The ionic charges are balanced by anionic ligands known from transition metal complex chemistry, e.g. hydride ions ($H^-$) or anions of inorganic or organic acids, e.g. $F^-$, $Cl^-$, $Br^-$ or $I^-$, fluorine complexes of the type $BF_4^-$, $PF_6^-$, $SbF_6^-$ or $AsF_6^-$, anions of oxygen acids, alcoholates or acetylides or anions of the cyclopentadiene anion type.

Anions of oxygen acids include, for example, sulfate, phosphate, perchlorate, perbromate, periodate, antimonate, arsenate, nitrate, carbonate, anions of $C_1$–$C_8$carboxylic acids, e.g. formate, acetate, propionate, butyrate, benzoate, phenylacetate, mono-, di- or tri-chloro-acetate or -fluoroacetate, sulfonates, e.g. mesylate, ethanesulfonate, propanesulfonate or n-butanesulfonate, trifluoromethanesulfonate (triflate) or benzenesulfonate or benzyl-sulfonate, which can be substituted by $C_1$–$C_4$alkyl, $C_1$–$C_4$alkoxy or by halogen, especially by fluorine, chlorine or by bromine, e.g. tosylate, brosylate, p-methoxy- or p-ethoxy-benzenesulfonate, pentafluorobenzenesulfonate or 2,4,6-triisopropylbenzenesulfonate, phosphonates, e.g. methyl-, ethyl-, n-propyl- or n-butyl-phosphonate, phenylphosphonate, p-methylphenylphosphonate or benzylphosphonate, and $C_1$–$C_{12}$alcoholates, e.g. methanolate or ethanolate.

Neutral and anionic ligands can be present up to the preferred coordination number, especially four, five or six. Negative total charges are balanced by cations, for example monovalent cations, e.g. $Na^+$, $K^+$, $NH_4^+$ or $(C_1$–$C_4alkyl)_4 N^+$.

Suitable neutral ligands are known from transition metal complex chemistry. They are coordinated with the coordination centre with emphasis on different types of bond, e.g. σ, π, µ, η bonds or combinations thereof up to the preferred coordination number of the complex cation. Suitable ligands are selected from the group comprising aqua ($H_2O$), amino, nitrogen, carbon monoxide, nitrosyl, phosphines, e.g. $(C_6H_5)_3P$, $(iso-C_3H_7)_3P$, $(C_5H_9)_3P$ or $(C_6H_{11})_3P$, amines, e.g. ethylenediamine, ethylenediaminotetraacetate (EDTA), N,N-dimethyl-N',N'-bis(2-dimethylaminoethyl)ethylenediamine ($Me_6TREN$), catechol, N,N'-dimethyl-1,2-phenyldiamine, 2-(methylamino)phenol, 3-(methylamino)-2-butanol, N,N'-bis(1,1-dimethylethyl)-1,2-ethanediamine or N,N,N',N",N"-pentamethyldiethyltriamine (PMDETA), $C_1$–$C_8$glycols or glycerides, e.g. ethylene glycol or propylene glycol or derivatives thereof, e.g. di-, tri- or tetraglymes, and monodentate or bidentate heterocyclic e⁻ donor ligands.

Heterocyclic e⁻ donor ligands are derived, for example, from unsubstituted or substituted hetero-arenes from the group comprising furan, thiophene, pyrrole, pyridine, bispyridine, picolylimine, γ-pyran, γ-thiopyran, phenanthroline, pyrimidine, bis-pyrimidine, pyrazine, indole, coumarin, thionaphthene, carbazoles, dibenzofuran, dibenzothiophene, pyrazole, imidazole, benzimidazole, oxazole, thiazole, bisthiazole, isoxazole, isothiazole, quinoline, bisquinoline, isoquinoline, bisisoquinoline, acridine, chroman, phenazines, phenoxazines, phenothiazines, triazines, thianthrene, purine, bis-imidazole and bisoxazole.

Following the polymerisation reaction, the polymerisate (V) can be isolated or reacted, preferably in situ, with an N→O compound of formula

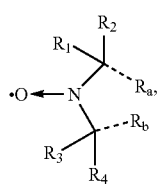

(VIII)

which corresponds to the group of partial formula $A_0$ and wherein $R_1$–$R_4$ and $R_a$ and $R_b$ are as defined above, and the N→O-substituted polymer or block copolymer (VII) prepared. Isolation of the polymerisate can be carried out, for example, according to known methods, for example distillation and removal of unreacted monomers by filtration.

The invention relates also to the use of a polymer or block copolymer (V) in the preparation of polymers or block copolymers (VII) wherein .X is replaced by an open-chain or cyclic group R'R"N—O..

After the substitution of the polymerisate by the N→O compound (VIII), the transition metal complex catalyst is separated off, the solvent is removed by evaporation or the N→O-group-substituted polymer (VII) is precipitated from a suitable liquid phase, and the polymer is filtered off and washed and then dried.

The elimination of the leaving group —X, e.g. halogen, and the substitution of the polymerisate by the N→O compound (VIII) are carried out, for example, by dissolving the polymerisate (V) in a solvent and adding the N→O compound (VIII). The reaction can be carried out in a temperature range of from room temperature to the boiling temperature of the reaction mixture, preferably from room temperature to 100° C.

Since the polymerisation and subsequent derivatisation with an N→O compound (VIII) according to the ATRP method have the characteristics of a "living" polymerisation reaction, it is possible to start and end the polymerisation reaction as desired. The block co-polymers (V) and (VII) obtainable according to the process have low polydispersity. It is preferable to obtain a polydispersity of from 1.01 to 2.2, preferably from 1.01 to 1.9, especially from 1.01 to 1.5.

N→O compounds (VIII) are known. They are commercially available or can be prepared according to the processes mentioned in U.S. Pat. Nos. 5,204,473 and 4,581,429 and the publications cited therein.

The ATRP process and its various advantages are described, for example, in the publication by K. Matyjaszewski in ACS Symp. Ser. Vol. 685 (1998), pp. 2–30. The polymers and copolymers can be processed further according to customary processes and in most cases can be used without further purification steps. This is advantageous if the batches are to be scaled-up with a view to industrial application.

The invention relates also to all N→O-substituted polymers or block copolymers that can be prepared using α-halocarboxylic acid esters (I), an N→O compound of formula VIII and the ATRP method. The invention relates to all products-by-process, even where they do not come under the definitions of formula VII above or where formula VII does not correctly define the structure of the products-by-process.

The invention relates also to a polymer composition comprising a polymer or block copolymer (V), wherein $R_1$, $R_2$, A, B, x, y and m are as defined, and additives customarily present in polymer compositions.

The invention relates also to polymer compositions comprising a polymer or block copolymer (V) in admixture with an N→O-substituted polymer or block copolymer (VII) and additives customarily present in polymer compositions.

Such additives can be added in small amounts, e.g. UV absorbers or light stabilisers, for example from the series of hydroxyphenylbenzotriazoles, hydroxyphenylbenzophenones, oxalamides and hydroxyphenyl-s-triazines. Especially suitable are light stabilisers from the group of so-called sterically hindered amines (HALS), e.g. of the 2-(2-hydroxyphenyl)-1,3,5-triazine or 2-hydroxyphenyl-2H-benzotriazole type. Examples of light stabilisers of the 2-(2-hydroxyphenyl)-1,3,5-triazine type are known from the patent literature, e.g. U.S. Pat. No. 4,619,956, EP-A-434,608, U.S. Pat. No. 5,198,498, U.S. Pat. No. 5,322,868, U.S. Pat. No. 5,369,140, U.S. Pat. No. 5,298,067, WO-94/18278, EP-A-704,437, GB-A-2,297,091 or WO-96/28431.

The compositions may comprise further customary additives, for example fillers, e.g. calcium carbonate, silicates, glass or glass fibre material, talcum, kaolin, mica, barium sulfate, metal oxides and hydroxides, carbon black, graphite, powdered wood and powdered or fibrous material of other natural products, synthetic fibres, plasticisers, lubricants, emulsifiers, pigments, flow auxiliaries, catalysts, optical brighteners, flame-retardants, antistatics and blowing agents.

The composition can contain the mentioned polymers in concentrations of about from 0.01 to 99.0% by weight, preferably from 0.1 to 95% by weight, especially from 1.0 to 90.0% by weight, more especially from 5.0 to 80.0% by weight, based on the monomer content of the composition.

The invention relates also to a polymer composition comprising
a) a polymer or block copolymer (V),
   wherein $R_1$, $R_2$, A, B, x, y and m are as defined above; and
b) a further polymer or oligomer of formula $$A_x\text{-}B_y \qquad (IX),$$

wherein
A and B are polymer blocks of ethylenically unsaturated monomer units and x and y denote the number of monomer units in the blocks A and B, one value of x and y being zero and the other value being an integer greater than zero, or both values x and y being integers greater than zero.

The invention relates also to a polymer composition comprising
a') an N→O-substituted polymer or block copolymer (VII) and
b') a further polymer or oligomer (IX).

The compositions can contain the mentioned customary additives and the polymer or oligomer components a) and b), or a') and b'), in concentrations of about from 0.01 to 99.0% by weight, preferably from 0.1 to 95% by weight, especially from 1.0 to 90.0% by weight, more especially from 5.0 to 80.0% by weight, based on the monomer content of the composition.

The polymers and the compositions according to the present invention can be used for a very wide variety of technical applications, for example as adhesives, detergent adjuvants, detergents, dispersants, emulsifiers, surfactants, antifoams, tackifiers, corrosion inhibitors, viscosity improvers, lubricants, flow improvers, thickeners, crosslinking agents, as additives for water treatment, electronic materials, paints and lacquers, coatings, inks, photo developers, superabsorbents, cosmetics, preservatives, or as biocides or modifiers and adjuvants for asphalt, textiles, ceramics and wood.

EXAMPLES

Example 1

Preparation of the Compound:

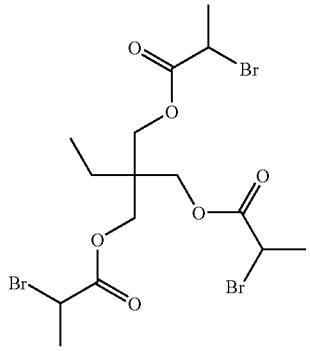

Starting Materials:

26.84 g (0.2 mol) of 1,1,1-(tris-hydroxymethyl)-propane (Fluka, purum); 136.4 g (0.6 mol) of 2-bromopropanoyl bromide (Fluka, pract. 95%); 47.5 g (0.6 mol) of pyridine (Fluka, puriss. p.a.); 500 ml of THF (Fluka, puriss. p.a.); 1500 ml sulfonating flask having a reflux condenser and mechanical stirring apparatus.

A solution of 2-bromopropanoyl bromide in 180 ml of THF is added dropwise over the course of 45 minutes, with cooling to 10–15° C., to a solution of 1,1,1-(tris-hydroxymethyl)-propane and pyridine in 320 ml of THF (slightly exothermic reaction). The reaction mixture is then heated at 60° C. for 3 hours and then cooled and filtered. Dilution is carried out with 500 ml of tert-butyl methyl ether and extraction is carried out twice with 150 ml of water each time until the reaction becomes neutral. The organic phase is dried over $Na_2SO_4$, filtered and concentrated completely in a rotary evaporator. Crude yield: 116.95 g. The crude product is purified by column chromatography (silica gel, toluene as eluant): Yield of pure product: 70.48 g (65%).

| Elemental analysis: | | |
| --- | --- | --- |
| C | H | Br |
| 33.69[1] | 4.30[1] | 44.47[1] |
| 33.63[2] | 4.22[2] | 44.60[2] |

[1]calculated;
[2]found

Example 2

Preparation of the Compound

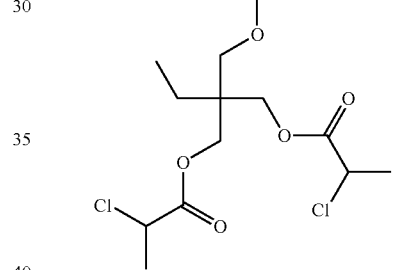

Starting Materials:

26.84 g (0.2 mol) of 1,1,1-(tris-hydroxymethyl)-propane (Fluka, purum); 76.18 g (0.6 mol) of 2-chloropropanoyl chloride (Fluka, pract. 97%); 47.5 g (0.6 mol) of pyridine (Fluka, puriss. p.a.); 500 ml of THF (Fluka, puriss. p.a.); 1500 ml sulfonating flask having a reflux condenser and mechanical stirring apparatus.

Analogously to Example 1, 66.32 g (82%) of pure product are obtained.

| Elemental analysis: | | |
| --- | --- | --- |
| C | H | Cl |
| 44.41[1] | 5.71[1] | 26.21[1] |
| 44.09[2] | 5.34[2] | 26.45[2] |

[1]calculated;
[2]found

Example 3

Preparation of the Compound

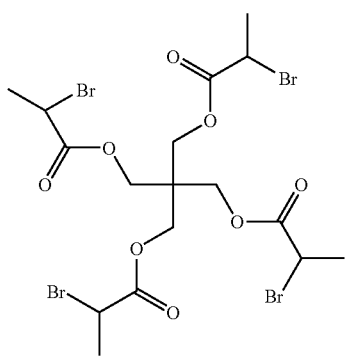

Starting Materials:

27.20 g (0.2 mol) of pentaerythritol (Fluka, purum); 181.7 g (0.8 mol) of 2-bromopropanoyl bromide (Fluka, pract. 97%); 63.2 g (0.8 mol) of pyridine (Fluka, puriss. p.a.); 500 ml of THF (Fluka, puriss. p.a.); 1500 ml sulfonating flask having a reflux condenser and mechanical stirring apparatus.

The procedure is analogous to Example 1. The crude product (150 mg) is purified by recrystallisation from isopropanol. 35.48 g (26%) of pure product are obtained. Melting point: 95° C.;

| Elemental analysis: | | |
|---|---|---|
| C | H | Br |
| 30.21[1] | 3.58[1] | 47.30[1] |
| 30.70[2] | 3.61[2] | 45.28[2] |

[1]calculated;
[2]found

Example 4

Preparation of the Compound

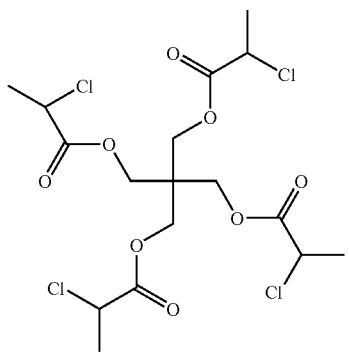

Starting Materials:

2.72 g (0.02 mol) of pentaerythritol (Fluka, purum); 10.15 g (0.08 mol) of 2-chloropropanoyl chloride (Fluka, pract. 97%); 6.32 g (0.08 mol) of pyridine (Fluka, puriss. p.a.); 50 ml of THF (Fluka, puriss. p.a.); 100 ml sulfonating flask having a reflux condenser and mechanical stirring apparatus.

Analogously to Example 3 (1/10 batch), 6.10 g (48%) of pure product are obtained; melting point: 84° C.

| Elemental analysis: | | |
|---|---|---|
| C | H | Cl |
| 40.72[1] | 4.82[1] | 28.28[1] |
| 40.98[2] | 4.60[2] | 28.45[2] |

[1]calculated;
[2]found

Example 5 a) Preparation of a "3-Star" Polymerisate having a low Molecular Weight

Starting Materials:

30.76 g (0.24 mol) of n-butyl acrylate (Fluka, purum); 0.57 g (4.0 mmol) of Cu(I)Br (Fluka, purum washed with acetic acid and dried); 0.52 g (3.0 mmol) of N,N,N',N'',N''-penta-methyldiethylenetriamine (Fluka, purum); 10.78 g (20.0 mmol) of 1-(2-bromopropionyl-oxy)-2-bis(2-bromopropionyloxymethyl)butane (initiator Example 1); 30.76 g of dioxane (Fluka, puriss. p.a.); 150 ml sulfonating flask having a reflux condenser, mechanical stirrer and dropping funnel; connections for vacuum and $N_2$.

Cu(I)Br and the monomer n-butyl acrylate are weighed into the reaction vessel, 20 g of dioxane are added and the vessel is degassed several times by evacuation and flushing with $N_2$. The ligand former PMDETA (N,N,N',N'',N''-pentamethyldiethylenetriamine) is added, and evacuation and flushing with $N_2$ are effected again. By immersion in an oil bath (85° C.), the mixture is heated to 50° C., at which temperature the initiator (Example 1), dissolved in 10.76 g of dioxane, is added rapidly from the dropping funnel. The strongly exothermic polymerisation reaction commences at about 85° C. with the temperature rising rapidly. By cooling using an ice bath, the temperature is maintained at 95–100° C. A conversion of 100% is achieved after 20 minutes' polymerisation time ($^1$H-NMR monitoring), and the reaction mixture is cooled and diluted with 50 ml of dioxane. 30 g of $Al_2O_3$ (Alox®) are added, and the mixture is stirred for 1 hour and filtered. The polymer solution is concentrated completely in vacuo at 80° C. in a rotary evaporator. Yield: 39.5 g (95%).

GPC (THF, PS standards): $M_n$=1700 (calculated: 2080), $M_w$=2160, PDI=1.27; MALDI-TOF MS: $M_n$=2030, $M_w$=2300, PDI=1.17;

| Elemental analysis: | | |
|---|---|---|
| C | H | Br |
| 57.27[1] | 8.07[1] | 11.54[1] |
| 57.26[2] | 8.26[2] | 11.44[2] |

[1]calculated;
[2]found b) Replacement of the Br Terminal Groups by 4-Benzoyloxy-TEMPO Starting Materials:

5.0 g (12.0 mmol Br terminal groups) of Br-substituted polymer Example 5 a); 3.31 g (12.0 mmol) of 4-benzoyloxy-TEMPO; 0.86 g (6.0 mmol) of CuBr; 2.07 g (12.0 mmol) of PMDETA; 7.5 ml of dioxane In a 25 ml three-necked flask having a magnetic stirrer, the mentioned reagents (without the ligand former PMDETA) are mixed under $N_2$, and the oxygen is expelled by evacuation and flushing with $N_2$ three times. The ligand former PMDETA is then added at room temperature and the mixture is heated in an oil bath to 65° C., during which the mixture rapidly changes colour from orange via black to green. The mixture is left to react for a further 4 hours at 65° C. and filtered. 10 ml of dioxane and four 5 g portions of aluminium oxide are then added (to adsorb the residual copper complex), with stirring each time and filtration through a suction filter each time. The solution is concentrated at 60° C. for 2 hours in a rotary evaporator, to yield 6.6 g (90%) of product.

GPC: $M_n$=2172 (calculated: 2290); $M_w$=2600; PDI=1.20; N content: 2.48%; Br content: <0.3%, which works out as a degree of replacement of more than 97.4%.

c) Preparation of a "3-Star" Polymerisate having a Relatively high Molecular Weight Starting Materials:

17.96 g (0.14 mol) of n-butyl acrylate (Fluka, purum); 0.111 g (0.8 mmol) of Cu(I)Br (Fluka, purum washed with acetic acid and dried); 0.139 g (0.8 mmol) of N,N,N',N",N"-pentamethyldiethylenetriamine (Fluka, purum); 2.10 g (3.9 mmol) of 1-(2-bromopropionyl-oxy)-2-bis(2-bromopionyloxymethyl)butane (initiator Example 1); 30.76 g of dioxane (Fluka, puriss. p.a.); 150 ml sulfonating flask having a reflux condenser, mechanical stirrer and dropping funnel; connections for vacuum and $N_2$.

Cu(I)Br and 14.0 g of the monomer n-butyl acrylate are weighed into the reaction vessel and the vessel is degassed several times by evacuation and flushing with $N_2$. The ligand former (N,N,N',N",N"-pentamethyldiethylenetriamine) is added, and evacuation and flushing with $N_2$ are effected again. By immersion in an oil bath (85° C.), the mixture is heated to 50° C., at which temperature the initiator, dissolved in 3.96 g of residual monomer, is added rapidly from the dropping funnel. The strongly exothermic polymerisation reaction commences at about 85° C., with the temperature rising rapidly. By cooling using an ice bath, the temperature is maintained at a maximum of 105° C. A conversion of 100% is achieved after 45 minutes' polymerisation time ($^1$H-NMR monitoring), and the reaction mixture is cooled and diluted with 50 ml of dioxane. 30 g of Alox® are added, and the mixture is stirred for 1 hour and filtered. The polymer solution is concentrated completely in vacuo at 80° C. in a rotary evaporator. Yield: 18.5 g (92%).

GPC (THF, PS standards): $M_n$=4890 (calculated: $M_n$=5150), $M_w$=6520, PDI=1.33;

Elemental analysis:

| C | H | Br |
|---|---|---|
| 62.23[1] | 8.90[1] | 4.65[1] |
| 62.25[2] | 8.84[2] | 4.43[2] |

[1]calculated;
[2]found d) Preparation of a "3-Star" Copolymerisate Comprising 1 st Block Poly(n-BA) and 2nd Block poly-DMAEA Starting Materials:

5.15 g of "3-star" polymerisate having a low molecular weight, Example 5 a); 0.71 g (5 mmol) of 2-dimethylaminoethyl acrylate (DMAEA, BASF, techn.); 72.0 mg (0.5 mmol) of Cu(I)Br (Fluka, purum washed with acetic acid and dried); 87.0 mg (0.5 mmol) of N,N,N',N",N"-pentamethyldiethylenetriamine (Fluka, purum); 25 ml round-bottomed flask having a magnetic stirrer and septum.

Cu(I)Br, the "3-star" polymerisate having a low molecular weight, Example 5 a), and DMAEA are weighed into the reaction vessel and the vessel is degassed several times by evacuation and flushing with $N_2$. The ligand former PMDETA is added, and evacuation and flushing with $N_2$ are effected again. By immersion in an oil bath, the mixture is heated to 50° C. and is left to react for 30 minutes, conversion of about 100% ($^1$H-NMR monitoring) being achieved. The mixture is cooled and diluted with 20 ml of ethyl acetate, 5 g of $Al_2O_3$ (Alox®) are added, and the mixture is stirred for 30 minutes and filtered. The polymer solution is concentrated completely (1 hour) at 80° C. in a rotary evaporator, to yield 5.0 g (85%) of product.

GPC (THF, PS standards): $M_n$=5590 (calculated: $M_n$=5870), $M_w$=7520, PDI=1.35

Elemental analysis:

| C | H | N | Br |
|---|---|---|---|
| 61.80[1] | 8.93[1] | 1.19[1] | 4.08[1] |
| 62.24[2] | 8.80[2] | 0.87[2] | 3.44 |

[1]calculated;
[2]found e) Preparation of a "3-Star" Copolymerisate Comprising 1 st Block Poly(n-BA) and 2nd Block poly-HEA Starting Materials:

5.15 g of "3-star" polymerisate having a low molecular weight, Example 5 a); 0.58 g (5 mmol) of 2-hydroxyethyl acrylate (DMAEA, BASF, techn.); 72.0 mg (0.5 mmol) of Cu(I)Br (Fluka, purum washed with acetic acid and dried); 87.0 mg (0.5 mmol) of N,N,N',N",N"-pentamethyldiethylenetriamine (Fluka, purum); 25 ml round-bottomed flask having a magnetic stirrer and septum.

Analogously to Example 5 d), 5.0 g (85%) of product are obtained.

GPC (THF, PS standards): $M_n$=6530 (calculated: $M_n$=5730), $M_w$=9690, PDI=1.48;

Elemental analysis:

| C | H | Br |
|---|---|---|
| 61.17[1] | 8.70[1] | 4.18[1] |
| 61.67[2] | 8.83[2] | 3.42[2] |

[1]calculated;
[2]found

Example 6 a) Preparation of a "4-Star" Polymerisate having a Low Molecular Weight

Starting Materials:

15.38 g (0.12 mol) of n-butyl acrylate (Fluka, purum); 0.28 g (2.0 mmol) of Cu(I)Br (Fluka, purum washed with acetic acid and dried); 0.35 g (2.0 mmol) of N,N,N',N'',N''-penta-methyldiethylenetriamine (Fluka, purum); 6.76 g (20.0 mmol) of 1,2,2,3-tetrakis(2-bromo-propionyloxymethyl)propane (initiator Example 3); 15.38 g of dioxane (Fluka, puriss. p.a.); 50 ml sulfonating flask having a reflux condenser, mechanical stirrer and dropping funnel; connections for vacuum and $N_2$.

Analogously to Example 5 a), the reactants are left to react at 90° C., a conversion of about 100% being obtained after 90 minutes' polymerisation time ($^1$H-NMR monitoring). 19.9 g (90%) of pure product are isolated.

GPC (THF, PS standards): $M_n$=1770, $M_w$=2080, PDI=1.17 (calculated: $M_n$=2210); MALDI-TOF MS: $M_n$=1920, $M_w$=2020, PDI=1.09;

| Elemental analysis: | | |
|---|---|---|
| C | H | Br |
| 54.79[1] | 7.65[1] | 14.44[1] |
| 55.29[2] | 7.58[2] | 13.26[2] |

[1]calculated;
[2]found b) Replacement of the Br Terminal Groups by 4-Hydroxy-TEMPO

Starting Materials:

5.0 g (8.3 mmol of Br terminal groups) of Br-substituted polymer Example 6 a); 1.43 g (8.3 mmol) of 4-hydroxy-TEMPO; 1.20 g (8.3 mmol) of CuBr; 1.91 g (8.3 mmol) of Me$_6$TREN of formula

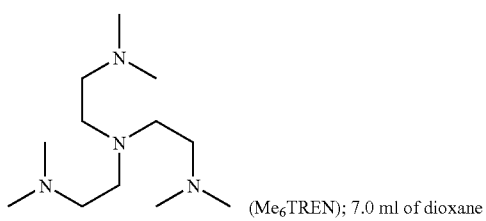

(Me$_6$TREN); 7.0 ml of dioxane

In a 25 ml three-necked flask having a magnetic stirrer, the mentioned reagents (without the ligand former Me$_6$TREN) are mixed under $N_2$, and the oxygen is expelled by evacuation and flushing with $N_2$ three times. The ligand former Me$_6$TREN is then added at room temperature, during which the mixture changes colour rapidly from orange via black to green and the temperature rises to 50° C. The reagents are left to react for a further 1 hour at room temperature and then filtration is carried out. 10 ml of dioxane and two 5.0 g portions of aluminium oxide are then added (to adsorb the residual copper complex), and the mixture is stirred and filtered through a suction filter. The solution is concentrated at 60° C. for 2 hours in a rotary evaporator, to yield 5.2 g (90%) of product.

GPC: $M_n$=2280 (calculated: 2140), $M_w$=2630, PDI=1.15

| Elemental analysis: | | | |
|---|---|---|---|
| C | H | N | Br |
| 63.70[1] | 9.36[1] | 2.17[1] | 0.00[1] |
| 62.45[2] | 9.21[2] | 1.72[2] | 1.13 |

[1]calculated;
[2]found

From the bromine content it is possible to calculate a degree of replacement of 91.5%.

c) Preparation of a "4-Star" Polymerisate having a Relatively high Molecular Weight Starting Materials:

269.4 g (2.1 mol) of n-butyl acrylate (Fluka, purum); 1.67 g (12.0 mmol) of Cu(I)Br (Fluka, purum washed with acetic acid and dried); 2.09 g (3.0 mmol) of N,N,N',N'',N''-pentamethyldiethylenetriamine (Fluka, purum); 39.54 g (20.0 mmol) of 1,2,2,3-tetrakis(2-bromopropionyloxymethyl)propane (initiator Example 3); 1000 ml sulfonating flask having a reflux condenser, mechanical stirring apparatus and a dropping funnel; connections for vacuum and $N_2$.

Analogously to Example 5 c), a conversion of about 100% is obtained after 45 minutes' polymerisation time ($^1$H-NMR monitoring) and, after treatment with $Al_2O_3$ in ethyl acetate, 297.0 g (96%) of pure product are isolated.

GPC (THF, PS standards): $M_n$=5080 (calculated: $M_n$=5290), $M_w$=6190, PDI=1.22

| Elemental analysis: | | |
|---|---|---|
| C | H | Br |
| 61.07[1] | 8.68[1] | 6.04[1] |
| 61.10[2] | 8.63[2] | 5.56[2] |

[1]calculated;
[2]found d) Preparation of a "4-Star" Copolymerisate Comprising 1st Block Poly(n-BA) and 2nd Block poly-DMAEA Starting Materials:

80.0 g of "4-star" polymerisate having a low molecular weight, Example 6 a); 10.74 g (75 mmol) of 2-dimethylaminoethyl acrylate (DMAEA, BASF, techn.); 1.08 g (7.5 mmol) of Cu(I)Br (Fluka, purum washed with acetic acid and dried); 1.23 g (7.5 mmol) of N,N,N',N'',N''-pentamethyldiethylenetriamine (Fluka, purum); 750 ml sulfonating flask having mechanical stirring apparatus and septum.

Cu(I)Br, the "4-star" polymerisate having a low molecular weight, Example 6 a), and DMAEA are weighed into the reaction vessel and the vessel is degassed several times by evacuation and flushing with $N_2$. The ligand former (N,N,N',N'',N''-pentamethyl-diethylenetriamine) is then added, and evacuation and flushing with $N_2$ are effected again. By immersion in an oil bath, the mixture is heated to 90° C. and left to react for 60 minutes, a conversion of about 100% being obtained ($^1$H-NMR monitoring). The mixture is cooled and diluted with 150 ml of ethyl acetate, 80.0 g of $Al_2O_3$ (Alox®) are added, and the mixture is stirred for 60 minutes and filtered. The polymer solution is concentrated completely (1 hour) at 80° C. in a rotary evaporator, to yield 76.6 g (85%) of product.

GPC (THF, PS standards): $M_n=5820$ (calculated: $M_n=5800$), $M_w=7410$, PDI=1.27

| Elemental analysis: | | | |
|---|---|---|---|
| C | H | N | Br |
| 60.79[1] | 8.74[1] | 1.17[1] | 5.33[1] |
| 61.36[2] | 8.86[2] | 1.04[2] | 4.16[2] |

[1]calculated;

[2]found e) Preparation of a "4-Star" Copolymerisate Comprising 1st Block Poly(n-BA) and 2nd Block poly-HEA Starting Materials:

80.0 g of "4-star" polymerisate having a low molecular weight, Example 6 a); 8.71 g (75 mmol) of 2-hydroxyethyl acrylate (HEA, BASF, techn.); 1.08 g (7.5 mmol) of Cu(I)Br (Fluka, purum washed with acetic acid and dried); 1.23 g (7.5 mmol) of N,N,N',N'',N''-pentamethyldiethylenetriamine (Fluka, purum); 750 ml sulfonating flask having mechanical stirring apparatus and septum.

Analogously to Example 6 d), 68.4 g (77%) of product are obtained.

GPC (THF, PS standards): $M_n=6880$ (calculated: $M_n=5660$), $M_w=9730$, PDI=1.41

| Elemental analysis: | | |
|---|---|---|
| C | H | Br |
| 60.15[1] | 8.51[1] | 5.45[1] |
| 60.96[2] | 8.66[2] | 4.27[2] |

[1]calculated;

[2]found

Example 7

Preparation of 1,3,5-Tris(2-Bromo-2-Methylpropanoyloxy) Benzene:

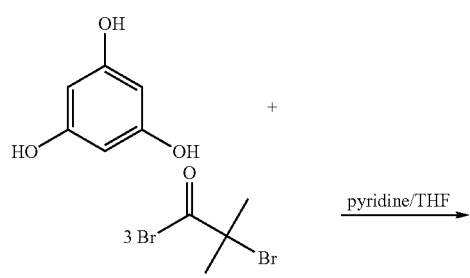

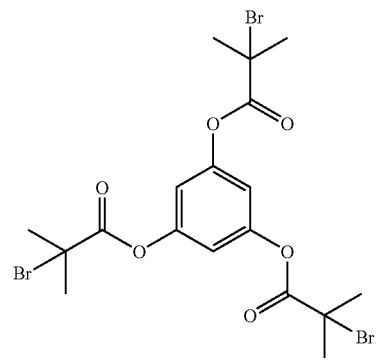

In a 100 ml round-bottomed flask, 5.0 g (39.6 mmol) of 1,3,5-trihydroxybenzene (Fluka, puriss) are dissolved in 40 ml of THF with stirring using a magnetic stirrer, and 9.40 g (118.8 mmol) of pyridine (Fluka, puriss) are added. The solution is cooled to 5° C. and 27.34 g (118.8 mmol) of α-bromo-isobutyric acid bromide (Fluka pract) dissolved in 20 ml of THF are added slowly with stirring over the course of 1 hour. After the addition, the mixture is stirred for a further one hour at 60° C., the suspension is left to cool to room temperature and filtered. The solvent is evaporated off using a rotary evaporator, and the residue is washed with water and recrystallised from isopropanol. Yield: 11.04 g (48.2%) of white crystals. Melting point of the product purified by thin-layer chromatography: 186.4° C.

| Elemental analysis: | | |
|---|---|---|
| C | H | Br |
| 37.72[1] | 3.69[1] | 41.82[1] |
| 38.10[2] | 3.56[2] | 41.51[2] |

[1]calculated;

[2]found

Example 8

Preparation of 1,2,3,4,5,6-Hexakis(2-Chloro-Propanoyloxy)-n-Hexane

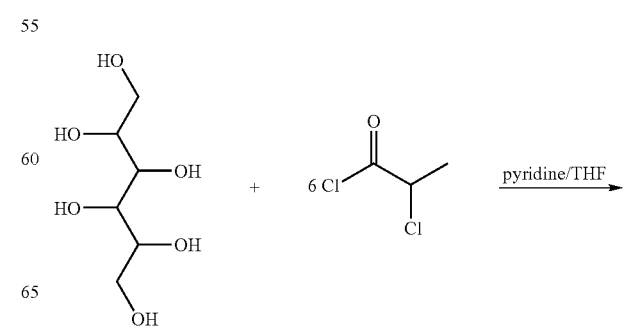

-continued

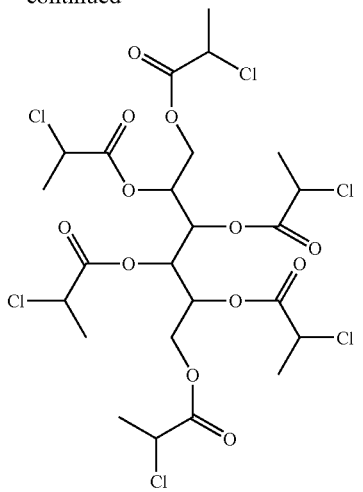

In a 100 ml round-bottomed flask, 5.0 g (27.4 mmol) of sorbitol (Fluka, puriss) are dissolved in 10 ml of THF with stirring using a magnetic stirrer, and 13.0 g (164.4 mmol) of pyridine (Fluka, puriss) are added. The solution is cooled to room temperature, and 23.35 g (164.4 mmol) of 2-chloropropanoyl chloride (Fluka, pract.) dissolved in 20 ml of THF are added slowly with stirring over the course of 1 hour. After the addition, the mixture is stirred for a further four hours at 60° C., and the suspension is left to cool to room temperature and then filtered. The solvent is evaporated off using a rotary evaporator, and the residue is dissolved in tert-butyl methyl ether, washed with water and filtered over activated carbon. The solvent is removed in vacuo at 0.05 mbar. Yield: 11.85 g (59.6%) of a yellowish oil. The oil is then purified by column chromatography ("flash" method) over silica gel. Yield of product purified by thin-layer chromatography: 7.02 g (35.3%).

Elemental analysis:

| C | H | Cl |
|---|---|---|
| 39.73[1] | 4.45[1] | 29.36[1] |
| 40.32[2] | 4.31[2] | 29.11[2] |

[1]calculated;
[2]found

Example 9

Preparation of a "3-Star" Polymerisate having a Relatively High Molecular Weight In a 25 ml round-bottomed flask provided with a septum and magnetic stirrer, 4.71 g (47 mmol) of methyl methacrylate (MMA, Fluka puriss) are polymerised under a nitrogen atmosphere as follows: the appropriate amounts of Cu(I)Br catalyst (Fluka, purum), the initiator 1,3,5-tris(2-bromo-2-methylpropanoyloxy)benzene, Example 7, the solvent (if required) and MMA are placed in the flask, which is sealed securely with a rubber septum. With stirring, the vessel is evacuated and flushed three times with nitrogen. The ligand former PMDETA (N,N,N',N'',N''-pentamethyidiethylenetriamine, Fluka, purum) is then added using a syringe. The vessel is heated in an oilbath to 90° C. and the progress of the reaction is monnitored by taking regular samples and by NMR monitoring in $CDCl_3$. The reaction conditions are described in Table 1:

TABLE 1

| No. | Initiator (mg) | Cu(I)Br (mg) | PMDETA (mg) | Solvent | Reaction time (h) | Conversion (%) | $M_n$ (calc.) |
|---|---|---|---|---|---|---|---|
| 1 | 67 | 34 | 41 | — | 0.33 | 69 | 28 100 |
| 2 | 22.3 | 11.2 | 13.5 | — | 3.0 | 60 | 72 500 |
| 3 | 13.5 | 6.7 | 8.1 | 3 ml dioxane | 5.5 | 50 | 101 000 |

Working up: After being taken up in 20 ml of ethyl acetate and filtered, the polymer is precipitated from 150 ml of ethanol. The polymerisate (poly(MMA)) is obtained in the form of a white powder after filtration and drying in vacuo at 50° C. Tab. 2 contains details relating to the yield and characteristic data, such as molecular weight determination by means of GPC (THF, PS standards) and light-scattering (LS, Wyatt Down DSP: "Multi Angle Laser Light Scatttering Instrument").

TABLE 2

| No. | Yield (%) | GPC: $M_n$ | GPC: $M_w$ | GPC: PDI | LS: $M_w$ | LS: PDI |
|---|---|---|---|---|---|---|
| 1 | 68.6 | 50 200 | 67 000 | 1.33 | 82 500 | 1.29 |
| 2 | 40.3 | 76 500 | 95 200 | 1.24 | 115 700 | 1.19 |
| 3 | 36.1 | 87 700 | 108 000 | 1.23 | 124 400 | 1.18 |

The PDI values are low and the higher $M_w$ value for the LS relative to that for the GPC indicates a compact molecular structure of those star-shaped macromolecules.

Example 10

Preparation of a Six-fold Branched Polymerisate having a Relatively High Molecular Weight In a 25 ml round-bottomed flask provided with a septum and magnetic stirrer, 4.71 g (47 mmol) of n-butyl acrylate (n-BA, Fluka puriss) are polymerised under a nitrogen atmosphere as follows: the appropriate amounts of Cu(I)Br catalyst (Fluka, purum), the initiator 1,2,3,4,5,6-hexakis(2-chloro-propanoyloxy)-n-hexane, Example 8, the solvent (if required) and n-BA are placed in the flask, which is sealed securely with a rubber septum. With stirring, the vessel is evacuated and flushed three times with nitrogen. The ligand former PMDETA (N,N,N',N'',N''-pentamethyldiethylenetriamine, Fluka, purum) is then added using a syringe. The vessel is heated in an oil bath to 90° C. and the progress of the reaction is monitored by taking regular samples and by NMR monitoring in CDCl$_3$. Table 3 describes sreaction conditions:

TABLE 3

| No. | Initiator (mg) | Cu(I)Cl (mg) | PMDETA (mg) | Reaction time (h) | Conversion (%) | $M_n$ (calc.) |
|---|---|---|---|---|---|---|
| 1 | 85 | 23.2 | 41 | 1.25 | 90 | 46 800 |
| 2 | 34.1 | 9.3 | 16.3 | 1.5 | 87 | 112 000 |
| 3 | 167 | 22.8 | 39.9 | 0.58 | 90 | 23 800 |

Working up: After dilution of the reaction mixture with 25 ml of ethyl acetate and the addition of 1.5 g of Al$_2$O$_3$ (adsorption of the catalyst), filtration and drying at 100° C. in vacuo (1 h, <0.4 mbar), poly(n-BA) is obtained in the form of an oil. Tab. 3 contains details relating to the yield and characterisation data, such as molecular weight determination by means of GPC (THF, PS standards) and light-scattering (LS, Wyatt Down DSP: "Multi Angle Laser Light Scattering ument").

TABLE 4

| No. | Yield (%) | GPC: $M_n$ | GPC: $M_w$ | GPC: PDI | LS: $M_w$ | LS: PDI |
|---|---|---|---|---|---|---|
| 1 | 84.7 | 38 700 | 47 100 | 1.22 | 49 400 | 1.17 |
| 2 | 87 | 98 400 | 135 300 | 1.32 | 146 600 | 1.28 |
| 3 | 90 | 24 000 | 33 800 | 1.41 | 39 400 | 1.32 |

The PDI values are low and the higher $M_w$ value for the LS relative to that for the GPC indicates a compact molecular structure of those star-shaped macromolecules.

Example 11

The initiator 1,2,2,3-tetrakis(2-bromopropionyloxymethyl)propane is prepared analogously to Example 3. n-Butyl acrylate (n-BA) is reacted with the initiator analogously to Example 5a to form the 4-armed star polymer: Characterisation: $M_n$=5080, $M_w$=6200, PDI=1.22, Br (found): 5.56%.

80.0 g of that 4-armed star-shaped poly-n-butyl acrylate and 1.08 g (7.5 mmol) of CuBr (Fluka, purified by washing with acetic acid) are placed in a 750 ml round-bottomed flask having a mechnical stirrer. The air is expelled by stirring and evacuation and flushing with nitrogen three times. 1.23 g (1.57 ml, 7.5 mmol) of PMDETA (Fluka/purum) are added through a septum using a syringe. The vessel is evacuated and flushed with nitrogen again. When the mixture becomes homogeneous as a result of stirring, the mixture is heated to 60° C. on an oil bath. 10.74 g (11.47 ml, 75 mmol) of 2-dimethylaminoethyl acrylate (BASF, technical grade) are added through the septum using a syringe. The temperature is raised to 90° C. over the course of one hour (polymerisation time). The conversion is determined by $^1$H-NMR analysis in CDCl$_3$ at about 100%. After cooling to room temperature, 150 ml of ethyl acetate and 80 g of neutral aluminium oxide (Aloxe for chromatography) are added. The polymer is obtained after stirring for 1 hour at room temperature, filtration and drying for one hour in a rotary evaporator at 80° C. under a high vacuum. Yield: 76.62 g (85%).

| Elemental analysis: | | | | |
|---|---|---|---|---|
| | C | H | N | Br |
| calculated | 60.79 | 8.74 | 1.17 | 5.33 |
| found | 61.36 | 8.86 | 1.04 | 4.16 |

Cu: 166 ppm (X-ray fluorescence);
GPC (THF): $M_n$ = 5800, $M_w$ = 7370, PDI = 1.27.

The invention claimed is:

1. A polymer or block copolymer of formula:

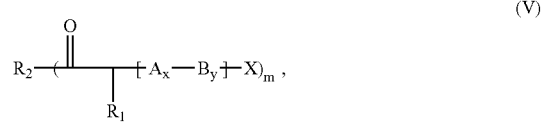

(V)

wherein
R$_1$ is Hydrogen, C$_1$–C$_4$Alkyl, Cyano, Phenyl or C$_1$–C$_4$Alkylphenyl;
R$_2$ is the radical of an acylated, branched, trihydric alcohol, the radical of a fully or partially acylated, linear or branched, tetrahydric alcohol, the radical of a fully or partially acylated, linear, penta- or hexahydric alcohol, the radical of a fully or partially acylated, linear or cyclic C$_4$–C$_6$aldose or C$_4$–C$_6$ketose or the radical of a fully or partially acylated disaccharide;
A and B are polymer blocks of ethylenically unsaturated monomer units selected from the group consisting of styrenes, acrolein, acrylic or methacrylic acid or salts thereof, acrylic or methacrylic acid anhydrides, acrylic or methacrylic acid C$_1$–C$_{24}$alkyl esters, acrylic or methacrylic acid mono- or di-C$_1$–C$_4$alkylamino-C$_2$–C$_4$alkyl esters, acrylic or methacrylic acid hydroxy-C$_2$–C$_4$alkyl esters, acrylic or methacrylic acid (C$_1$–C$_4$alkyl)$_3$silyloxy-C$_2$–C$_4$alkyl esters, acrylic or methacrylic acid (C$_1$–C$_4$alkyl)$_3$silyloxy-C$_2$–C$_4$alkyl esters, acrylic or methacrylic acid heterocyclyl-C$_2$–C$_4$alkyl esters, acrylic or methacrylic acid esters containing poly-C$_2$–C$_4$alkylene glycol ester groups, acrylic or methacrylic acid esters containing poly-C$_2$–C$_4$alkylene glycol ester groups esterified by substituted C$_1$–C$_{24}$alkoxy groups, acrylic or methacrylic acid amides, acrylic or methacrylic acid mono- or di-C$_1$–C$_4$alkylamides, acrylic or methacrylic acid amino-C$_2$–C$_4$alkylamides and acrylonitrile;
x and y denote the number of monomer units in the blocks A and B, one value of x and y being zero and the other value being an integer greater than zero, or both values x and y being integers greater than zero;
X is chlorine, bromine or iodine; and
m denotes an integer from three to six.

2. A block copolymer (V) according to claim 1, wherein $R_1$ is $C_1$–$C_3$alkyl or phenyl;

X is chlorine or bromine and $R_2$ is the radical of an acylated, branched, trihydric alcohol, the radical of an acylated, linear or branched, tetrahydric alcohol or the radical of a fully or partially acylated, linear, penta- or hexa-hydric alcohol, A and B are polymer blocks of ethylenically unsaturated monomer units selected from the group consisting of styrenes, acrolein, acrylic or methacrylic acid or salts thereof, acrylic or methacrylic acid anhydrides, acrylic or methacrylic acid $C_1$–$C_{24}$alkyl esters, acrylic or methacrylic acid mono- or di-$C_1$–$C_4$alkylamino-$C_2$–$C_4$alkyl esters, acrylic or methacrylic acid hydroxy-$C_2$–$C_4$alkyl esters, acrylic or methacrylic acid ($C_1$–$C_4$alkyl)$_3$silyloxy-$C_2$–$C_4$alkyl esters, acrylic or methacrylic acid ($C_1$–$C_4$alkyl)$_3$silyl-$C_2$–$C_4$alkyl esters, acrylic or methacrylic acid heterocyclyl-$C_2$–$C_4$alkyl esters, acrylic or methacrylic acid esters containing poly-$C_2$–$C_4$alkylene glycol ester groups, acrylic or methacrylic acid esters containing poly-$C_2$–$C_4$alkylene glycol ester groups esterified by substituted $C_1$–$C_{24}$alkoxy groups, acrylic or methacrylic acid amides, acrylic or methacrylic acid mono- or di-$C_1$–$C_4$alkylamides, acrylic or methacrylic acid amino-$C_2$–$C_4$alkylamides and acrylonitrile;

x and y denote integers greater than zero and represent the number of monomer units in the blocks A and B; and m is three or four.

3. A polymer composition comprising a polymer or block copolymer (V) according to claim 1, wherein $R_1$, $R_2$, A, B, x, y and m are as defined in claim 1, and at least one additive customary in polymer compositions.

4. A process for the preparation of a polymer or block copolymer (V), wherein $R_1$, $R_2$, A, B, X, x, y and m are as defined in claim 1, in which process ethylene-group-containing aliphatic monomers that form the basis of the polymer blocks A and B are subjected to a polymerisation reaction by atom transfer radical polymerisation (ATRP) in the presence of the α-halocarboxylic acid ester of the formula

(I)

as polymerisation initiator, wherein $R_1$, $R_2$ and X are as defined in claim 1, and in the presence of an oxidisable transition metal complex catalyst.

* * * * *